US012080388B1

United States Patent
Tal et al.

(10) Patent No.: US 12,080,388 B1
(45) Date of Patent: Sep. 3, 2024

(54) PANOMICS ONTOLOGY

(71) Applicant: Allscripts Software, LLC, Chicago, IL (US)

(72) Inventors: Shiri Ben Tal, Omer (IL); Assaf Halevy, Pittsburgh, PA (US); Joel Diamond, Pittsburgh, PA (US); Robert Wartenfeld, Moshav Ge+3 alya (IL); Eyal Greenberg, Meitar (FI); David Thomas Windell, Raleigh, NC (US)

(73) Assignee: 2bPrecise Technologies, LLC, Houston, TX (US)

( * ) Notice: Subject to any disclaimer, the term of this patent is extended or adjusted under 35 U.S.C. 154(b) by 0 days.

(21) Appl. No.: 15/230,264

(22) Filed: Aug. 5, 2016

Related U.S. Application Data

(60) Provisional application No. 62/201,554, filed on Aug. 5, 2015.

(51) Int. Cl.
| | |
|---|---|
| *G16H 10/60* | (2018.01) |
| *G06F 3/0488* | (2022.01) |
| *G06F 16/93* | (2019.01) |
| *G06F 3/04842* | (2022.01) |

(52) U.S. Cl.
CPC .......... *G16H 10/60* (2018.01); *G06F 3/0488* (2013.01); *G06F 16/93* (2019.01); *G06F 3/04842* (2013.01)

(58) Field of Classification Search
CPC .... G16H 10/20; G06F 3/0488; G06F 3/04842
See application file for complete search history.

(56) References Cited

U.S. PATENT DOCUMENTS

2015/0186618 A1* 7/2015 Poorvin ................ G16H 10/20
705/3

OTHER PUBLICATIONS

Sethi (Year: 2013).*

* cited by examiner

*Primary Examiner* — Aryan E Weisenfeld
(74) *Attorney, Agent, or Firm* — Calfee, Halter & Griswold LLP

(57) ABSTRACT

One or more preferred embodiments facilitate use of patient panomics indications to select treatments that will provide optimal results. One or more preferred embodiments relate to a practical ontology for the panomics domain that is utilized to support use of patient panomics indications. In accordance with one or more preferred implementations, a cancer panomics ontology facilitates replacement of traditional cancer stratification by organs (e.g. lung, breast, liver cancer) with cancer stratification by tumor biomarkers (e.g. HER2 mutations). In accordance with one or more preferred implementations, a panomic ontology is utilized to facilitate functionality of a precision medical system.

9 Claims, 14 Drawing Sheets

FIG. 10

PANOMICS ONTOLOGY

CROSS-REFERENCE TO RELATED APPLICATION

The present application is a U.S. nonprovisional patent application of, and claims priority under 35 U.S.C. § 119(e) to, U.S. provisional patent application Ser. No. 62/201,554, filed Aug. 5, 2015, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to healthcare and healthcare ontologies.

There is a growing emphasis in healthcare and medicine on what has been termed precision medicine. Precision medicine is a medical model that favors personalization of medical care, e.g. based on molecular or genomic information.

Genomic variation of cancer types is increasing rapidly as are targeted treatments. Although the amount of knowledge regarding genomic variation, affected pathways, and potential targeted treatments is expanding, this knowledge is typically not readily available at a treatment decision point and throughout management of a cancer patient.

Non-personalized cancer treatments lead to high costs and non-optimal outcomes. Mutations oriented targeted treatments are confined to known mutations for specific cancer types.

Moreover, there is frequently incomplete alignment between treating cancer and other patient comorbidities. There is a lack of adequate tools for comprehensive and omics-aware management of cancer patients.

Further, genomic related cancer research lacks longitudinal data regarding outcomes. Omics related cancer knowledge does not have a standardized terminology. Even traditional cancer knowledge does not have good standardized terminology today.

Further still, patients need better knowledge and engagement in their own treatment.

Needs exists for improvement in healthcare and healthcare ontologies. These, and other needs, are addressed by one or more aspects of the present invention.

SUMMARY OF THE INVENTION

The present invention includes many aspects and features. Moreover, while many aspects and features relate to, and are described in a particular context, the present invention is not limited to use only in this context, as will become apparent from the following summaries and detailed descriptions of aspects, features, and one or more embodiments of the present invention.

Accordingly, one aspect of the present invention relates to a clinical semantic ontology related to precision medicine for providing a new taxonomy for cancer terminology.

Another aspect relates to a method comprising intercepting, by health information exchange software loaded on a computing device, context information from electronic healthcare record software loaded on the computing device, the context information including an identification of a patient, and displaying, via an electronic display associated with the computing device, an HIE graphical interface overlaying an interface of the EHR software, the HIE graphical interface displaying information for the identified patient loaded based on the intercepted context, receiving, via one or more input devices associated with the computing device, user input corresponding to engagement with an interface element of the HIE graphical interface, and, in response thereto, launching oncology decision support software loaded on the computing device and running a query for relevant protocols for the identified patient utilizing data for the identified patient from the HIE software, and saving, in a unified patient record of the HIE software for the identified patient, one or more protocols from the oncology decision support software that were located by the executed query. The protocols that were located by the executed query were determined utilizing a panomics ontology providing cancer stratification by tumor biomarkers.

In a feature of this aspect, the computing device comprises a touchscreen device.

In a feature of this aspect, the computing device comprises a phone.

In a feature of this aspect, the computing device comprises a mobile device.

In a feature of this aspect, the computing device comprises a desktop computer.

In a feature of this aspect, the computing device comprises a laptop computer.

In a feature of this aspect, the one or more input devices comprise a mouse.

In a feature of this aspect, the one or more input devices comprise a keyboard.

In a feature of this aspect, the electronic display comprises a touchscreen, and the one or more input devices comprise the touchscreen.

Another aspect relates to a system comprising electronic healthcare record (EHR) software loaded on a computing device; health information exchange (HIE) software loaded on the computing device; oncology decision support software loaded on the computing device; wherein the HIE software is configured to intercept context information from the EHR software, the context information including an identification of a patient, and display an HIE graphical interface overlaying an interface of the EHR software, the HIE graphical interface displaying information for the identified patient loaded based on the intercepted context, receive user input corresponding to engagement with an interface element of the HIE graphical interface, and, in response thereto, launch the oncology decision support software and run a query for relevant protocols for the identified patient utilizing data for the identified patient from the HIE software, and save, in a unified patient record of the HIE software for the identified patient, one or more selected protocols from the oncology decision support software that were located by the executed query. The system is configured to query for protocols for a patient utilizing a panomics ontology providing cancer stratification by tumor biomarkers.

Another aspect relates to a system comprising health information exchange (HIE) software loaded on the computing device; oncology decision support software loaded on the computing device; wherein the HIE software is configured to intercept context information from electronic healthcare record software loaded on the computing device, the context information including an identification of a patient, and display an HIE graphical interface overlaying an interface of the EHR software, the HIE graphical interface displaying information for the identified patient loaded based on the intercepted context, receive user input corresponding to engagement with an interface element of the HIE graphical interface, and, in response thereto, launch the oncology decision support software and run a query for relevant protocols for the identified patient utilizing data for the identified patient from the HIE software, and save, in a unified patient record of the HIE software for the identified patient, one or more selected protocols from the oncology decision support software that were located by the executed query. The system is configured to query for protocols for a patient utilizing a panomics ontology providing cancer stratification by tumor biomarkers.

Another aspect relates to using results of precision medicine in combination with clinical data to provide clinical decision support at the point of care. In a feature, this includes parsing a flat file of clinical recommendations provided by a decision support system, comparing their precision-based records with clinical data and looking for interactions and/or incompatible treatment. In a feature, this includes parsing a flat file of clinical recommendations provided by a precision medicine or omics source such as an omics system.

Another aspect relates to using precision medicine along with comorbidity information to alert a physician of potential matches to clinical trials within a workflow.

Another aspect relates to using information within a clinical record to identify risk for a protocol, treatment, or care plan. In a feature of this aspect, the information comprises family history, social history, demographic information, prior treatment information, results information, medication information, allergy information, or comorbidity information. In a feature of this aspect, the protocol, treatment, or care plan comprises medication or procedures, such as testing, surgery, inpatient, or outpatient procedures. In a feature of this aspect, the protocol, treatment, or care plan comprises outpatient, aftercare, or homecare treatment such as physical therapy.

Another aspect relates to using similar results of precision medicine/treatment plans from a master patient database to guide a provider in decision making during diagnostics or selection of future treatment, matching specific mutations or other panomics with a current patient to improve treatment.

Another aspect relates to using simulations of treatment plans based on prior results, precision medicine, and statistical/probability-based information to guide selection of treatment or diagnosis.

Another aspect relates to providing open services that allow clinical, panomics, and genetic data to be utilized for research (cross continuum).

Another aspect relates to using a combination of financial (e.g. payer, etc.) information, panomics, and clinical (e.g. EHR or HIE) data to guide a treatment plan or future path. In one or more preferred implementations, this avoids wasted effort/time/patient emotion on treatments not compatible with a patient's financial means or payer coverage, helping organizations view cost effectiveness of treatments, etc.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIG. 10 illustrates omics report documents attached to a patient record;

DETAILED DESCRIPTION

Figure 1:
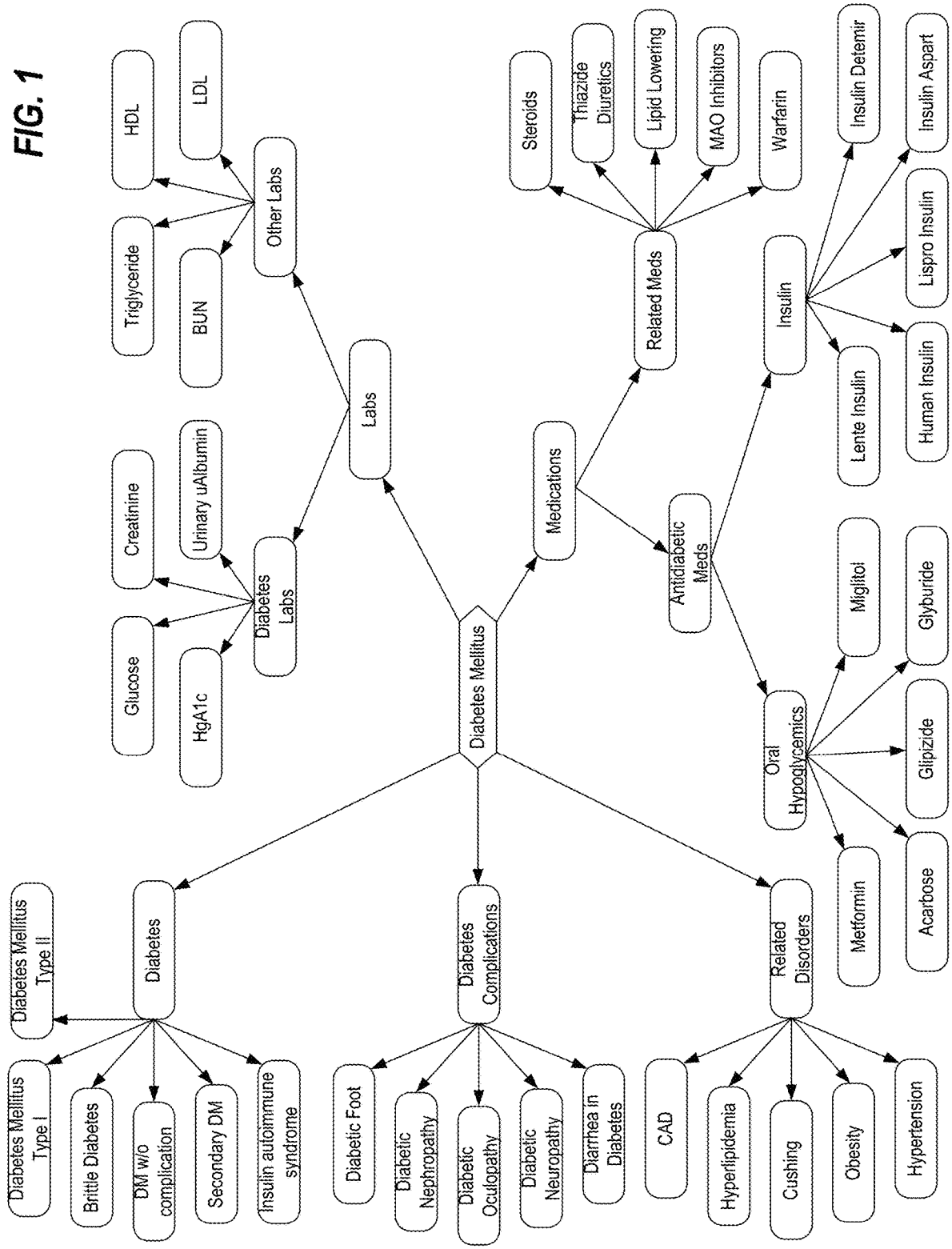
FIG. 1 illustrates a traditional ontology related to a diabetes semantic neighborhood.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

As noted above, there is a growing emphasis in healthcare and medicine on what has been termed precision medicine. One or more preferred embodiments facilitate use of patient panomics indications to select treatments that will provide optimal results. Panomics indications include, for example, data from molecular biology technologies such as genomics, proteomics, metabolomics transcriptomics, etc., or the integration of their combined use.

Ontologies are commonly used throughout healthcare provision. For example, FIG. 1 illustrates a traditional ontology related to a diabetes semantic neighborhood.

One or more preferred embodiments relate to a practical ontology for the panomics domain that is utilized to support use of patient panomics indications. In accordance with one or more preferred implementations, a panomics ontology includes both cancer and non-cancer panomics concepts, with relations to related insights, traditional cancer types, and clinical concepts.

Figure 2:
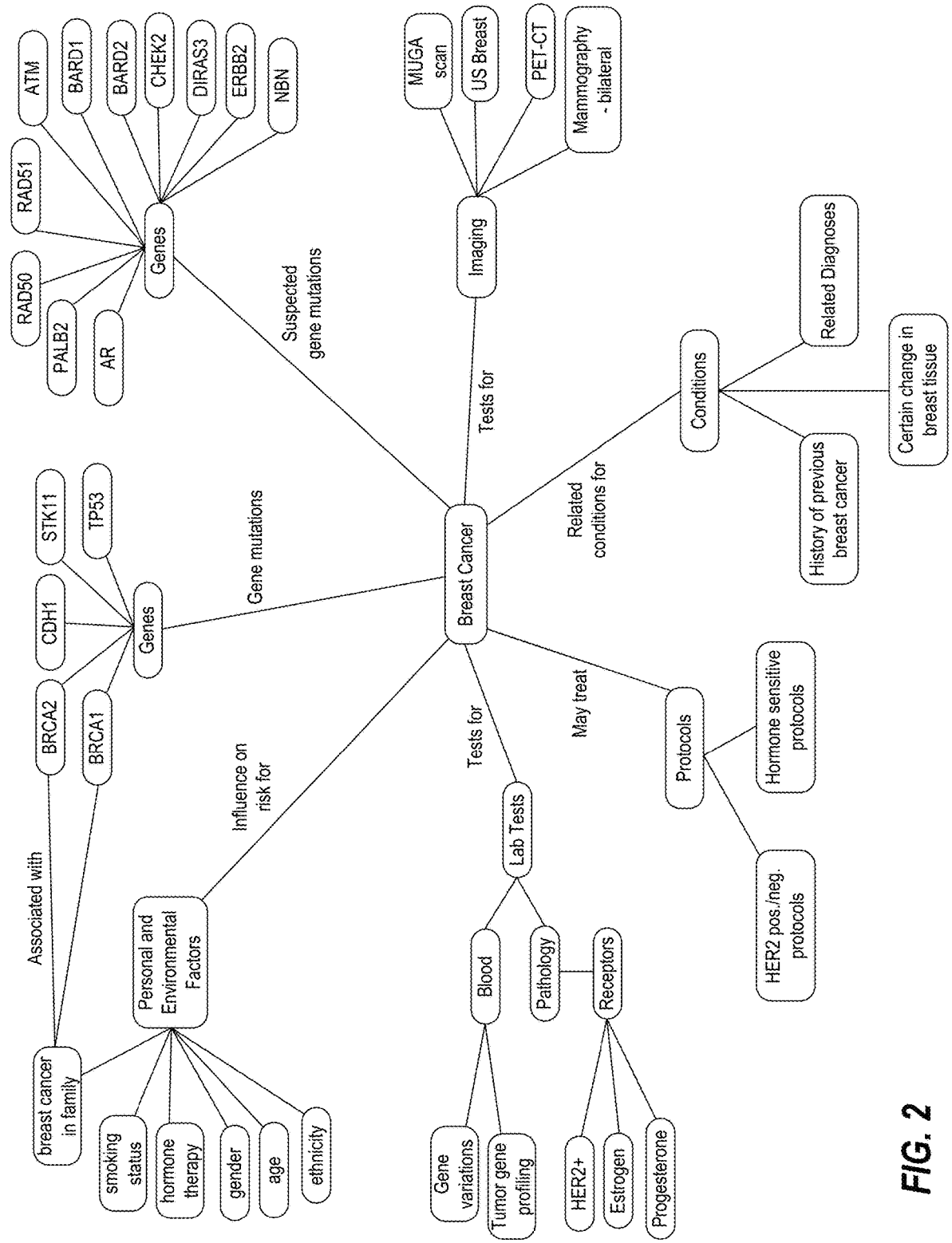
FIG. 2 illustrates an exemplary ontology related to a breast cancer semantic neighborhood in accordance with one or more preferred embodiments.

For example, FIG. 2 illustrates an exemplary ontology related to a breast cancer semantic neighborhood in accordance with one or more preferred embodiments. In accordance with one or more preferred implementations, a cancer panomics ontology facilitates or creates new standards for care and management of cancer patients.

In accordance with one or more preferred implementations, a cancer panomics ontology facilitates replacement of traditional cancer stratification by organs (e.g. lung, breast, liver cancer) with cancer stratification by tumor biomarkers (e.g. HER2 mutations).

Figure 3:
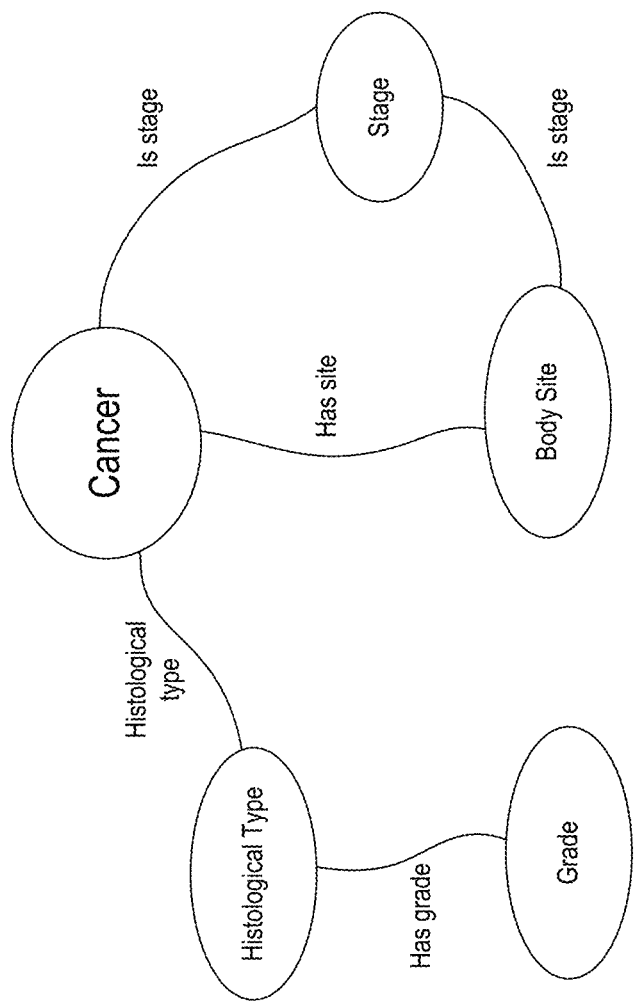
FIG. 3 illustrates a traditional cancer ontology.

FIG. 3 illustrates a traditional cancer ontology. The traditional ontology is designed to convey information regarding body sites (e.g. lung, breast, liver), histological types (e.g. carcinoma, leukemia, lymphoma, myeloma, sarcoma, mesothelioma), grades, and stages, as well as relationships between such data. For example, using the traditional ontology, a patient's cancer might be described as having a histological type of carcinoma, and a grade of II.

Figure 4:
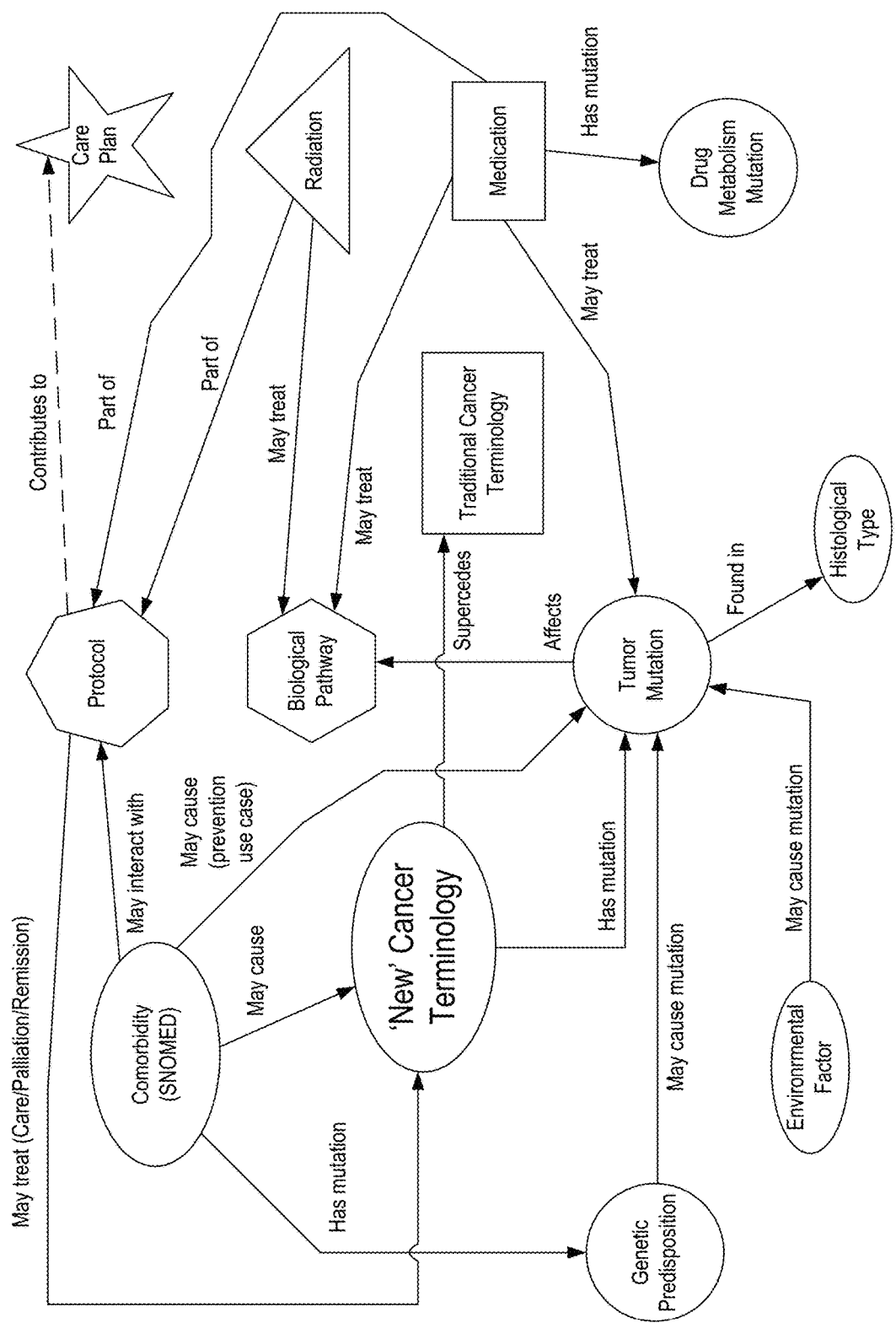
FIG. 4 illustrates an exemplary panomics ontology in accordance with one or more preferred implementations.

FIG. 4 illustrates an exemplary panomics ontology in accordance with one or more preferred implementations that relates clinical concepts with panomics concepts to create a semantic neighborhood for cancer treatment and for a preventive treatment approach.

Although FIG. 4 illustrates one exemplary panomics ontology in accordance with one or more preferred implementations, other potential panomics ontologies and variations thereof are contemplated as well.

One or more preferred embodiments relate to a precision medicine system that introduces an integrated, evidence-based, personalized approach to healthcare solutions that includes actionable clinical data and insights, enabling physicians to make informed decisions from complex genomic and proteomic analysis. In accordance with one or more preferred implementations, targeted treatments can be improved, for example, by applying genome sequencing and RNA sequencing that might uncover previously unknown mutations for a specific patient.

In accordance with one or more preferred implementations, a panomics ontology is utilized to facilitate functionality of a precision medical system.

Figure 5:
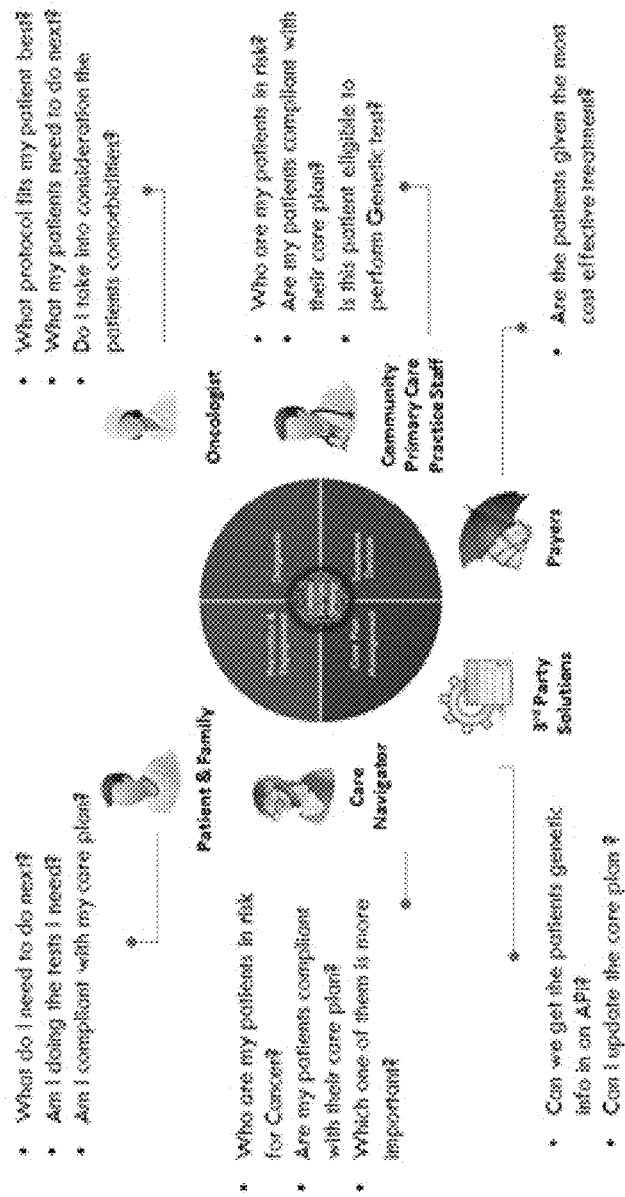
FIG. 5 illustrates exemplary questions various stakeholders may have that can be answered by a precision medicine system in accordance with one or more preferred implementations.

FIG. 5 illustrates exemplary questions various stakeholders may have that can be answered by a precision medicine system in accordance with one or more preferred implementations.

In accordance with one or more preferred implementations, a precision medicine system provides prevention and engagement functionality. This includes, for example, the ability to identify populations at risk by their clinical, social and genetic information. In accordance with one or more preferred implementations, severity scores are determined and utilized. This further includes the ability to monitor risk by genomic sequencing and precision medicine. This further includes point of care risk notifications. Preferably, the system enables and provides population monitoring. Further, the system preferably facilitates patient engagement in a prevention program.

In accordance with one or more preferred implementations, a precision medicine system provides precision diagnostic functionality. This includes, for example, functionality related to eligibility for sequencing, ordering of sequencing services, and omics aware diagnoses. This further includes functionality related to creation and management of a diagnostic care plan to manage engaged care (tests, referrals, results), as well as point of care recommendations to perform sequencing of a cancer specimen.

In accordance with one or more preferred implementations, a precision medicine system provides precision treatment decision functionality. This includes, for example, functionality related to omics and comorbidities aware treatment planning, Omics-Clinical-Financial precision decision support, and a cross payer-provider decision support system. This further includes functionality related to determining potential treatment protocols based on sequencing results. In accordance with one or more preferred implementations, a precision treatment plan enables comparison and simulation of protocols. Preferably, precision treatment decision functionality further includes functionality related to optimization of treatment by cost and outcomes, and functionality related to eligibility for clinical trials.

In accordance with one or more preferred implementations, a precision medicine system provides care plan management functionality. This includes, for example, functionality related to a point of care precision care plan, comorbidities care management, patient monitoring (e.g. a cancer patient) for regiment compliance, and treatment re-evaluation and recommendations. This further includes functionality to prioritize populations based on their cancer types, omics information and protocols, and functionality to monitor populations and proactively follow their care plan along with their comorbidities status. In accordance with one or more preferred implementations, functionality is provided by a care plan management web application, and/or a population management web application. In accordance with one or more preferred implementations, functionality is provided for the automatic creation of a care plan based on chosen protocol templates. Preferably, functionality is provided to identify and stratify patients (e.g. cancer patients) by risk, gaps in care, care plan, etc. In accordance with one or more preferred implementations, alerts are derived from or based on care plans and care plan management. In accordance with one or more preferred implementations, functionality is provided for comorbidity management and oncology views.

In accordance with one or more preferred implementations, a precision medicine system provides patient engagement functionality. This includes, for example, tools for the patient to allow for better care plan management and increase treatment plan adherence. This further includes functionality related to insights on potential treatment protocols, and patient-provider communication tools. This preferably further includes functionality which allows a patient to engage in social networking with other similar patients. Preferably, patient engagement functionality is provided or facilitated by a patient mobile application and/or a patient web portal. Preferably, functionality is provided to allow care plan access by a patient. Preferably, alerts and notifications are provided on care plan interventions. In accordance with one or more preferred implementations, precision patient education is provided (e.g. explanation regarding the meaning of a genetic test and treatment options).

In accordance with one or more preferred implementations, a precision medicine system provides analytics, pharma, and research enablement functionality. This preferably enables services to third party analytics platforms for organizations to better analyze, forecast and enforce the utilization of omics services and their impact on costs and outcomes. This preferably further enables acquisition of Omics-Clinical patient information to pharma companies. In accordance with one or more preferred implementations, an application programming interface is provided for interoperability. In accordance with one or more preferred implementations, data export functionality is provided, preferably with anonymization functionality for pharma and research.

In accordance with one or more preferred implementations, a precision medicine system provides OPEN functionality. This includes, for example, functionality which enables web services and APIs to 3rd parties to get and set information to and from the system.

Figure 6:
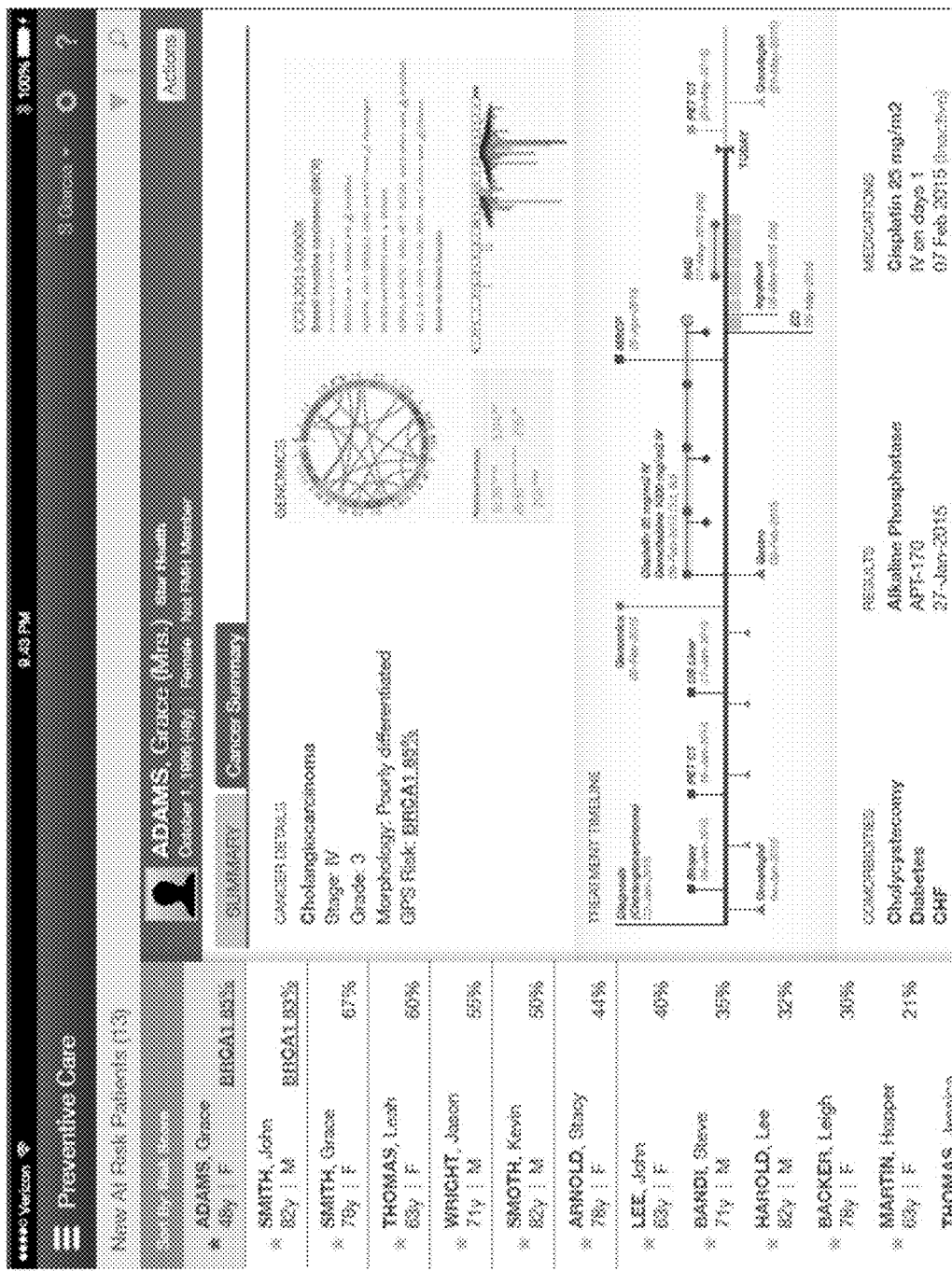
FIG. 6 illustrates an exemplary interface of a system in accordance with one or more preferred implementations.

In accordance with one or more preferred implementations, functionality of a precision medicine system is facilitated by enriching a patient record with discrete omics and cancer related data (mutations, insights, treatments, biomarkers, stage, grade, etc.). FIG. 6 illustrates an exemplary interface of a system in accordance with one or more preferred implementations.

In one or more preferred implementations, omics—cancer—care plan interoperability is enabled through data modeling and use of a panomic ontology. Preferably, patient oncology insights are acquired based on the sequencing and interpretation of omics labs. Additionally, in accordance with one or more preferred implementations, treatment planning and monitoring functionality is provided. In accordance with one or more preferred implementations, such treatment planning and monitoring is based on a recommendation from the platform, or from another system or platform, such as a decision support system or platform. In accordance with one or more preferred implementations, functionality is provided to acquire additional data from documents (e.g. pathology data through natural language processing).

In accordance with one or more preferred implementations, functionality of a precision medicine system is facilitated by enriching omics ability to interpret sequencing results utilizing patient outcomes and other clinical data across the continuum. In one or more preferred implementations, functionality is provided to acquire semantically harmonized relevant patient data (e.g. pathology data, labs, comorbidities). Further, preferably, functionality is provided to enable continuous feedback of the patient's clinical state. For example, this might include population health calculated insights about a patient's outcomes and survivability, treatment progress (e.g. plan vs. actual), and condition progress. Further still, preferably, functionality is provided for unstructured data mining (e.g. methods to extract relevant information from a document into a discrete form using NLP services), and analytics insights (e.g. patients with similar profiles). In accordance with one or more preferred implementations, a feedback mechanism and learning processes are provided.

In accordance with one or more preferred implementations, systems and software providing various functionality will operate together as part of a system or platform providing enhanced functionality.

Exemplary implementations will now be considered with respect to a platform comprising component systems including (1) a decision support and protocol adviser system (such as an oncology decision support system), (2) an electronic health records (EHR) system and/or health information exchange (HIE) system, and (3) an omics system.

The omics system provides omics, or panomics, information, e.g. by performing DNA or RNA sequencing, and provides omics based treatment recommendations.

The decision support and protocol adviser system provides for the matching of protocols to conditions. Traditionally decision support and protocol adviser systems are launched as a separate application. For example, a traditional cancer decision support and protocol adviser system might be launched as a separate application, require a user to log in, select a cancer type manually (main filter) or refine the search with fields such as pathology, stage, biomarker, gender and others. A user can select a protocol, but the selected protocol is traditionally not documented or integrated with an EHR.

The EHR or HIE system includes clinical patient data. In accordance with one or more preferred implementations, an HIE system and/or agent is utilized which is designed to sit on top of existing EHR software in an EHR agnostic manner. Such an HIE system is disclosed, for example, in U.S. Patent Application Pub. No. 2012/0215560, which patent application publication is hereby incorporated herein by reference. In accordance with one or more preferred implementations, an HIE system aggregates data from a plurality of sources, including a plurality of EHR systems. In accordance with one or more preferred implementations, the HIE system includes an HIE agent which comprises a graphical interface designed to overlay an EHR interface and provide information that may not be present in the EHR. The HIE system preferably intercepts context from an EHR application (such as a current patient for which data is being displayed), and uses such intercepted context to select data for display in an agent interface.

Figure 7:
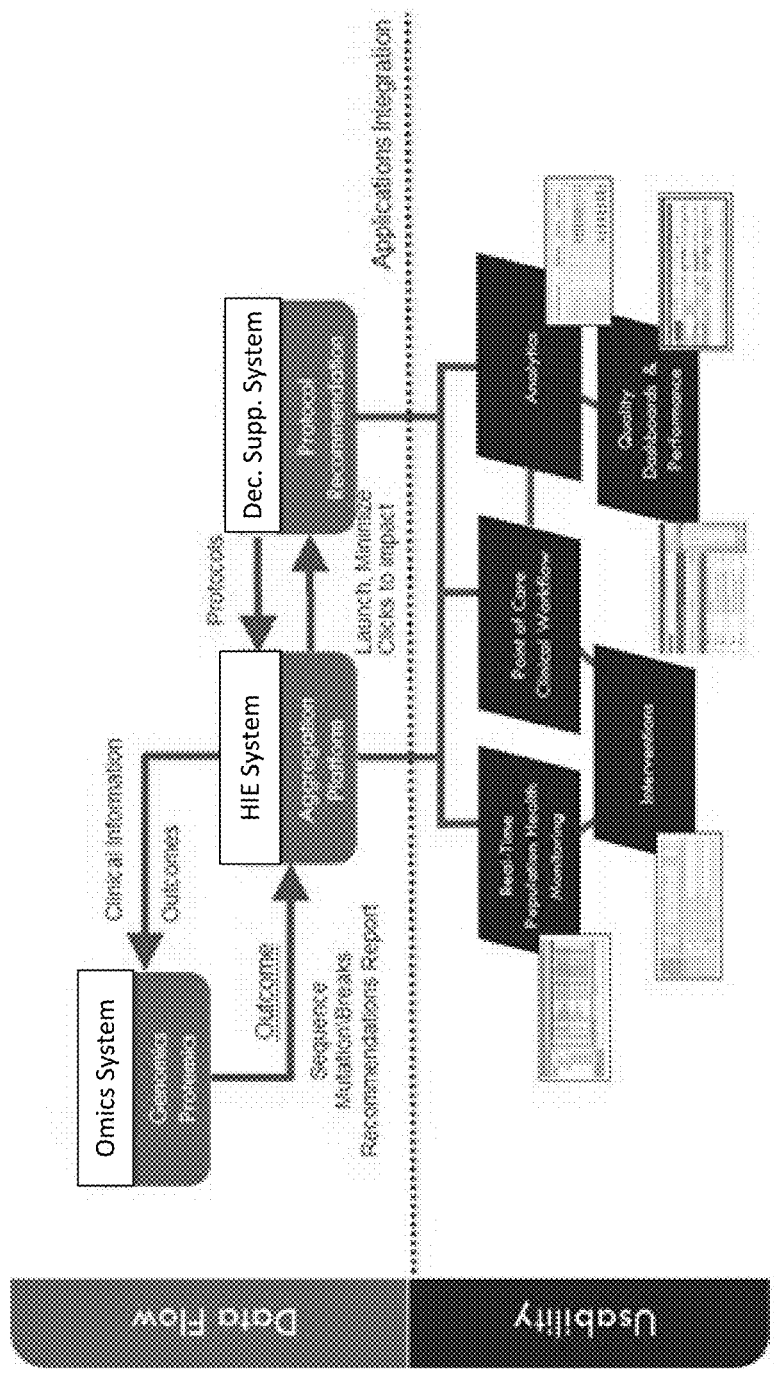
FIG. 7 illustrates systems integrated together via one or more interoperability connections.

In one or more preferred implementations, the systems are integrated together via one or more interoperability connections, as illustrated in FIG. 7.

Figure 8:
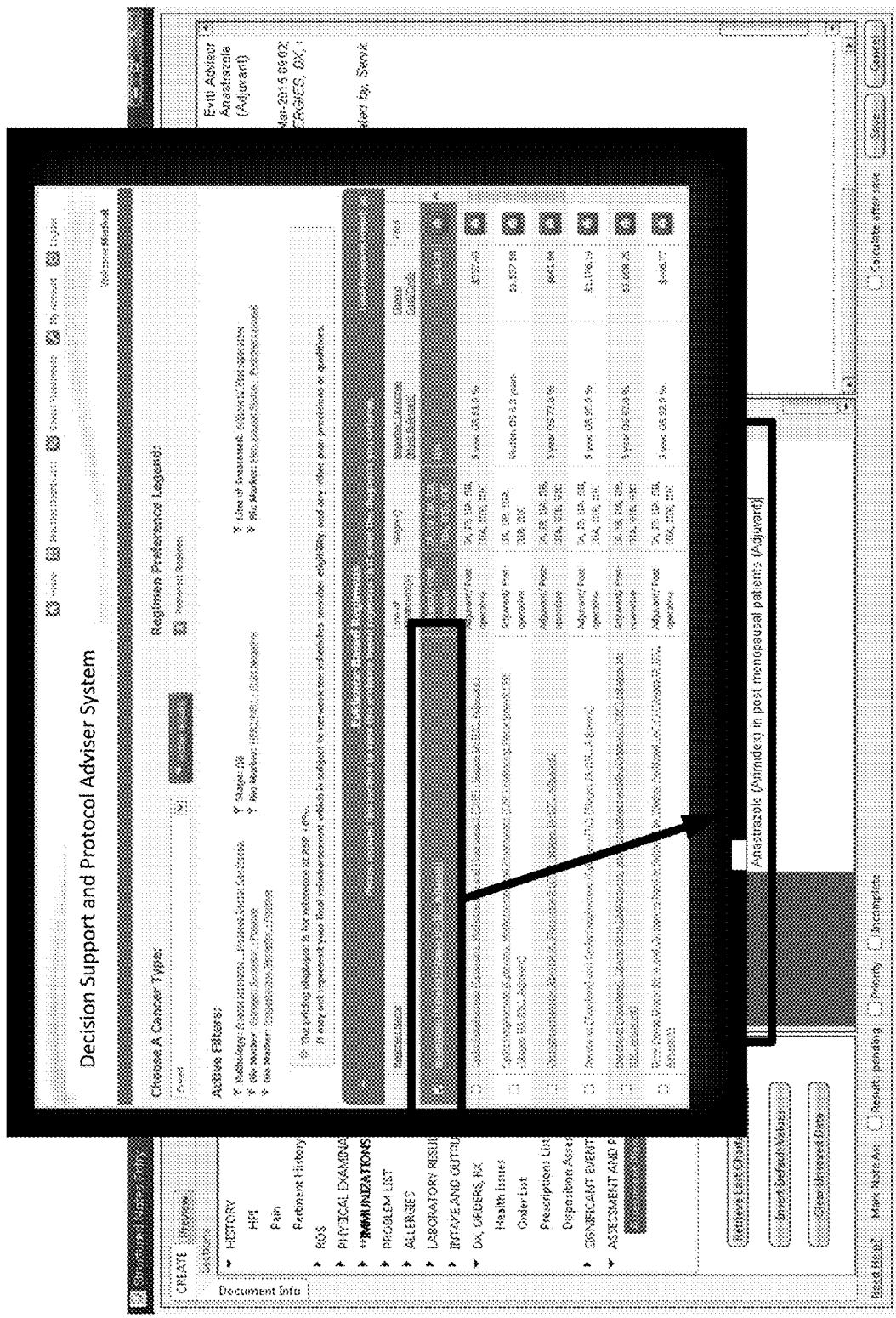
FIG. 8 illustrates an exemplary interface of a decision support and protocol adviser system which has been launched from an EHR or HIE system.

In one or more preferred implementations, the EHR or HIE system is configured to be able to launch the decision support and protocol adviser system from the EHR or HIE system. FIG. 8 illustrates an exemplary interface of a decision support and protocol adviser system which has been launched from an EHR or HIE system.

Figure 9:
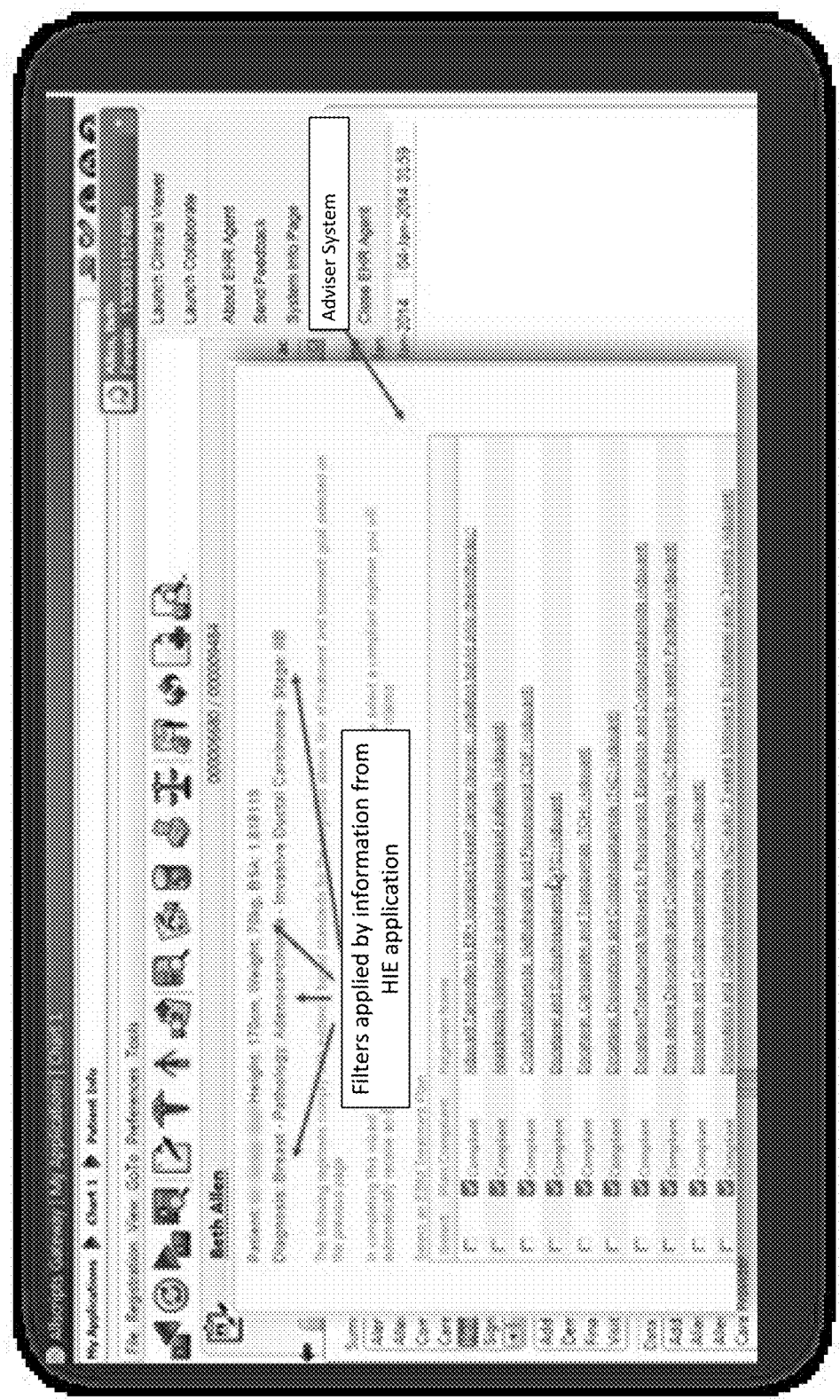
FIG. 9 illustrates the results of a query for possible protocols.

Preferably, the decision support and protocol adviser system can be launched in context using information (e.g. patient record information) from the EHR or HIE system (e.g. the decision support and protocol adviser system is launched and one or more query fields automatically populated based on clinical data from the EHR or HIE system). In accordance with one or more preferred implementations, a query for possible protocols can even be performed automatically, as illustrated in FIG. 9.

In one or more preferred implementations, the systems are configured such that one or more selected protocols from the decision support and protocol adviser system can be imported (e.g. automatically or manually) into the EHR or HIE system (as illustrated in FIG. 8). For example, a selected protocol or indication thereof can be saved as part of a patient record as a document, or added to an EHR progress note or an HIE care plan item.

Figure 10:
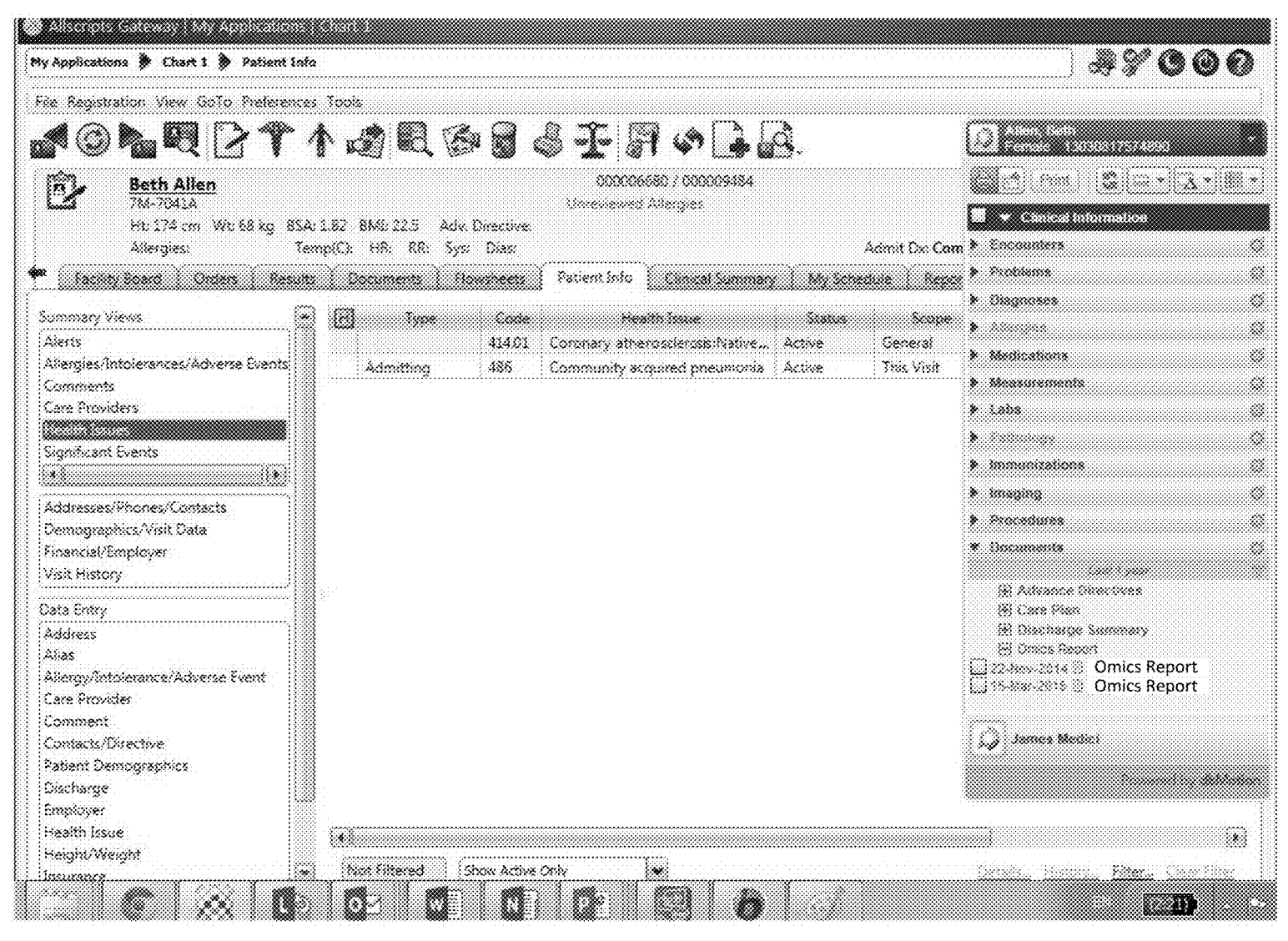
Figure 11:
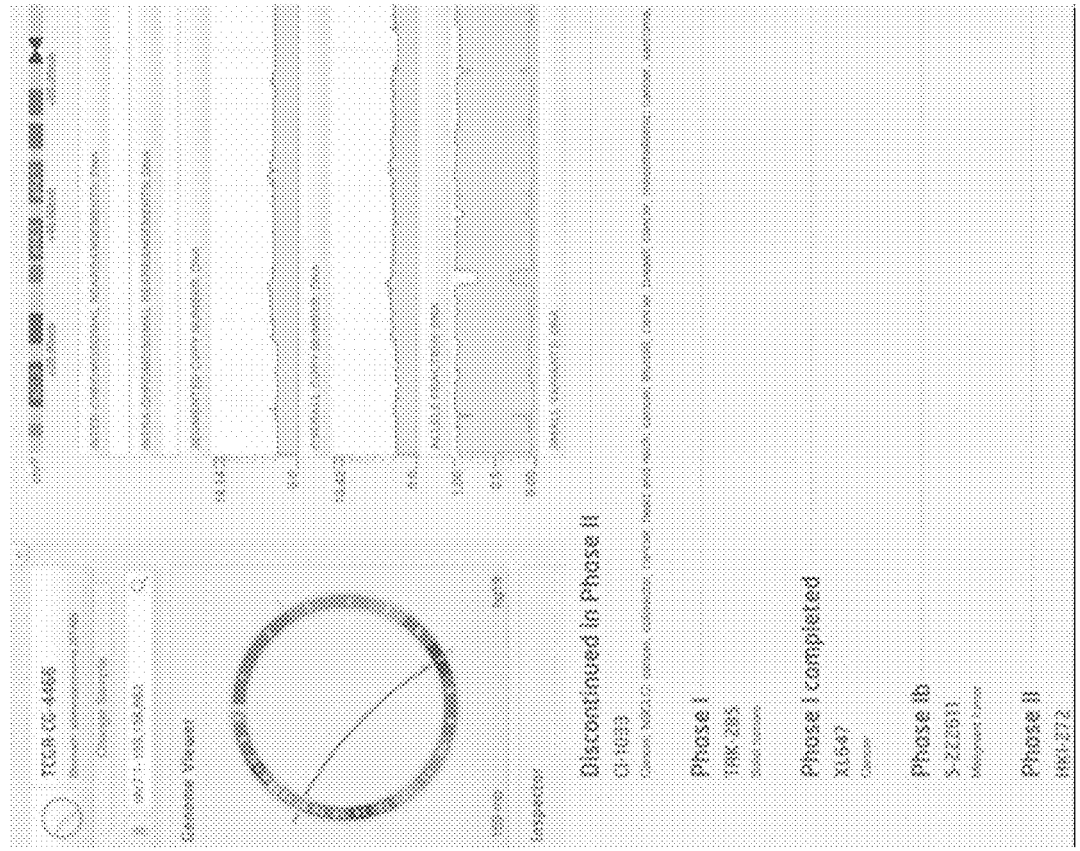
FIG. 11 illustrates a portion of an exemplary omics report document in the form of a PDF document.

In one or more preferred implementations, the systems are configured such that omics information (e.g. an omics report) from the omics system can be imported (e.g. automatically or manually) into a patient record of the EHR or HIE system for point of care availability (e.g. as a document, or as data to be included in fields of the record). For example, FIG. 10 illustrates omics report documents attached to a patient record, and FIG. 11 illustrates a portion of an exemplary such omics report document in the form of a PDF document which has been opened. In accordance with one or more preferred implementations, a patient record of an EHR or HIE system is enriched with discrete omics and/or cancer related data (e.g. mutations, insights, treatments, biomarkers, stage, grade, etc.).

In one or more preferred implementations, the systems are configured such that longitudinal data from the EHR or HIE system (e.g. clinical and outcome data) is provided to the omics system.

One challenge faced by traditional omics systems is a lack of information about what happened with a patient before and after an omics report. Information such as demographic data (e.g. gender, race, date of birth, height, weight, etc.), family history, prior cancer details, pathology details, current medications, and outcome indications are critical feedbacks that enable an omics system to improve omics based recommendations and protocols. In accordance with one or more preferred implementations, clinical and outcome data is utilized to improve omics based recommendations and protocols. In accordance with one or more preferred implementations, such improvement occurs automatically in a learning process, while in one or more preferred implementations an omics teams works to improve omics based recommendations and protocols based on such data.

In accordance with one or more preferred implementations, a system enables an omics system or team to improve omics based recommendations and protocols through outcome and patient clinical data across a continuum, such as pathology details (stage, grade), treatment information (plan vs. actual), outcomes, toxicity details, disease progression, and progress notes.

In accordance with one or more preferred implementations, an HIE system provides to an omics system or team semantically harmonized longitudinal patient data including pathology data, outcome data (e.g. related to "survivability"), treatments, comorbidity, condition progress, labs, and other information.

In accordance with one or more preferred implementations, population health insights represent calculated information required as feedback to omics recommendations.

In accordance with one or more preferred implementations, unstructured data mining methods are utilized to extract relevant information from a document into a discrete form using natural language processing services.

In accordance with one more preferred implementations, determination of patients with a similar profile is facilitated and partially determined by a utilized panomics ontology.

In accordance with one or more preferred implementations, a precision medicine system comprising a decision support and protocol adviser system, an EHR and/or HIE system, and an omics system serves as an oncology solution providing: point of care oncology management; omics empowerment; oncology population health management (e.g. cancer disease packages); omics, clinical, and financial analytics; research and life science enablement. Preferably, the system utilizes and leverages a cancer panomics ontology.

In accordance with one or more preferred implementations, the solution also leverages an HIE system including an HIE agent which sits above a point of care EHR to empower a decision support and protocol adviser system to provide more accurate patient insights, workflow awareness protocols, and clinical trial eligibility alternatives.

In accordance with one or more preferred implementations, patient-centric insights are provided at a point of care by bringing omics reports and recommendations into the HIE system, as a document for point of care availability, and enriching a unified patient record with discrete omics and cancer related data (e.g. mutations, insights, treatments, biomarkers, stage, grade, etc.). This improves omics awareness in cancer treatment through intelligent point of care insights. Data in the HIE system can be utilized to find relevant protocols using a decision support and protocol adviser system (e.g. by launching the decision support and protocol adviser system and running a query utilizing data from the HIE system). Preferably, point of care recommendations are provided regarding the need to perform sequencing based on disease stage and outcomes.

The decision support and protocol adviser system preferably additionally provides information and recommendations regarding potential clinical trials, including eligibility of a patient for a trial, information about a clinical trial (e.g. a clinical trial in which a patient is participating). In one or more preferred implementations, a system includes a framework for an organization to add its own trial inclusion criteria.

In accordance with one or more preferred implementations, a precision medicine system allows selected protocols to be stored as a part of a patient record in an EHR or HIE system, and further allows for the creation and management of omics driven care plans (e.g. a care plan comprised of one or more protocols) together with standard protocols.

In accordance with one or more preferred implementations, clinical data regarding treatment by one or more providers is utilized (e.g. automatically or manually) to inform selection of a protocol and/or creation of a care plan.

In accordance with one or more preferred implementations, real time updates and alerts are available at a point of care (e.g. oncologist, emergency department, PCP, care navigator, etc.). In accordance with one or more preferred implementations, an update or alert may be provided based on a disruption in protocol, a side effect or contraindication (e.g. renal status, liver functions, white blood cell count), or a major event (e.g. venous thromboembolism or myocardial infarction).

Figure 12:
FIG. 12 illustrates an exemplary view in accordance with one or more preferred implementations.

In accordance with one or more preferred implementations, a precision medicine system comprises an oncology specific EHR agent (or a more general EHR agent which includes such oncology functionality) configured to meet oncology point of care needs. Preferably, such an oncology EHR agent is configured to provide dedicated oncology views that combine omics and clinical relevant insights. FIG. 12 illustrates an exemplary view in accordance with one or more preferred implementations.

Figure 13:
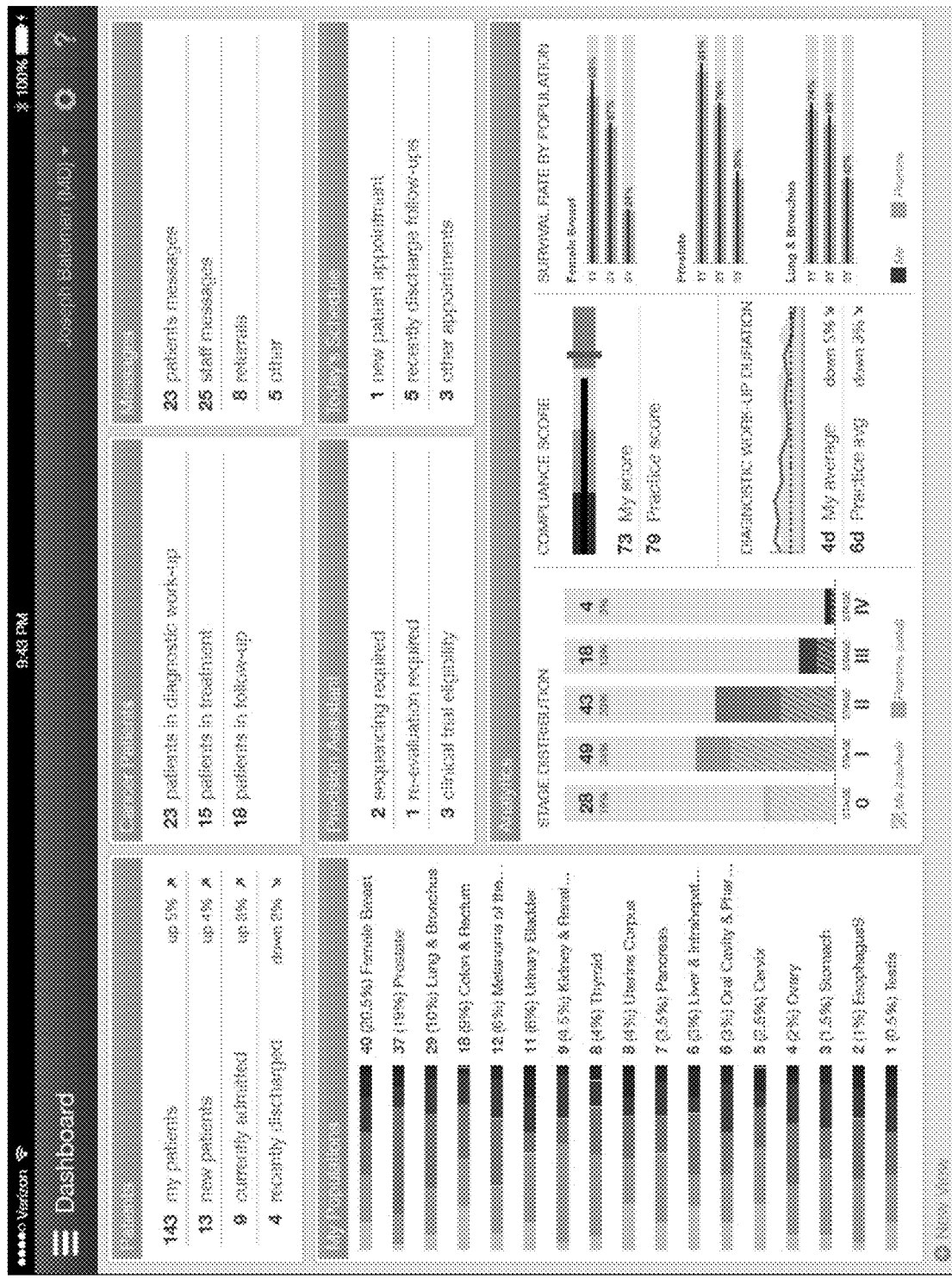
FIG. 13 illustrates an exemplary dashboard in accordance with one or more preferred implementations.

In accordance with one or more preferred implementations, a cancer population management system is provided to allow entities to better manage their cancer patients though tools for primary care, care navigator, and oncologists to stratify and prioritize populations based on their cancer conditions, omics information, and protocol based care plan information. Preferably, such a solution represents an end-to-end solution to manage cancer patients, increase omics aware treatment plans and increase omics based cancer recommendations. FIG. 13 illustrates an exemplary dashboard for such a solution.

In accordance with one or more preferred implementations, a cancer population management system enables monitoring of cancer populations and following of their care plans along with their comorbidities information.

In accordance with one or more preferred implementations, a cancer population management system provides functionality to define relevant cancer cohorts, such as, for example: gastroenterology cancer patients, colon cancer patients, FLT3 mutation patients, or patients on protocol X.

In accordance with one or more preferred implementations, a cancer population management system includes functionality to identify and stratify cancer patients population or patients at risk, provide recommendations for sequencing, provide scores (e.g. prediction scores or a severity scoring of cancer patients), provide comorbidities management, monitor relevant clinical data, events, gaps, protocol violation, care plan status and deviations, provide actionable ordering and tasking, provide patient tasking, providing messaging (e.g. provider-provider and patient-provider), track indicators (e.g. Myelotoxicity), identify gaps in care, identify deviations from protocol, track treatment results, identify unwanted events.

In accordance with one or more preferred implementations, a cancer population management system includes functionality to provide dynamic care plan management, including to generate a care plan derived from protocols (e.g. from a decision support and protocol adviser) and cancer type, provide a comprehensive longitudinal care plan view, provide care plan management capabilities by different providers, provide alerts on deviation from a care plan, monitor compliance, provide additional sequencing recommendations, and track patient engagement.

In accordance with one or more preferred implementations, one or more systems provide information to an analytics platform which utilizes omics-clinical and financial information to analyze cross-data financial information and outcomes. In accordance with one more preferred implementations, omics insights data is provided to insurers for tracking treatments and saving non-relevant treatments.

In accordance with one or more preferred implementations, omics and clinical data is combined for research, learning and creation of new insights and recommendations. In accordance with one or more preferred implementations, de-identified patient omics and clinical data is utilized for the purpose of pharmacogenomics research.

In accordance with one or more preferred implementations, omics—cancer—care plan interoperability is enabled through data modeling and a new ontology.

In accordance with one or more preferred implementations, a precision medicine system includes intelligent clinical-omics based data mining capabilities.

In one or more preferred implementations, search functionality is provided to allow a patient to utilize a patient portal to "patients like me" functionality to find patients sharing similar traits and connect via social networking to such patients.

In accordance with one or more preferred implementations, search functionality is provided to allow a provider or researcher to locate similar patients.

In accordance with one or more preferred implementations, a system provides global searching functionality to return semantically meaningful results in accordance with a panomics ontology. For example, if a search is performed for breast cancer, information regarding a BRCA1 mutation might be returned as a result as well.

Figure 14:
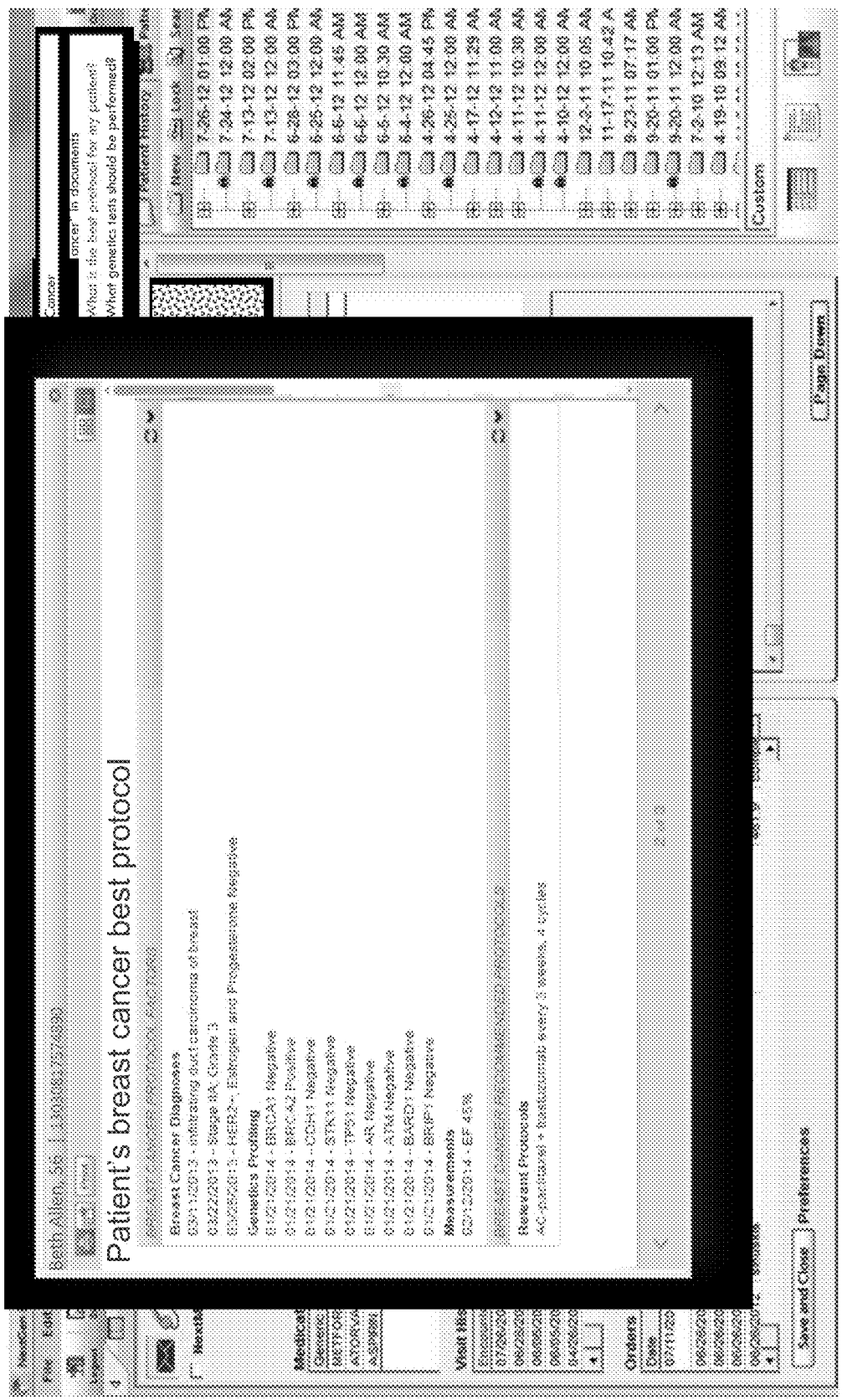
FIG. 14 illustrates exemplary intelligent question suggestion in accordance with one or more preferred implementations.

In accordance with one or more preferred implementations, a system is configured to intelligently suggest, and provide the answer to, questions related to diagnosis and treatment of conditions. For example, when a user goes to search for "cancer", the system might suggest the question "What is the best protocol for my patient?" or the question "What genetic tests should be performed?", as illustrated in FIG. 14. Preferably, the system is configured to provide answers to such questions if a user selects one of the suggested questions, or types in his or her own question.

In accordance with one or more preferred implementations, aspects and features disclosed herein serve to create a new foundation that enriches patient records, the omics recommendation process, and the protocols management process. In accordance with one or more preferred implementations, systems and methods serve to create better clinical standards of care and change the way providers treat and manage cancer patients by combining omics insights and longitudinal patient clinical outcomes. In accordance with one or more preferred implementations, systems and methods serve to change the way cancer patients are treated and managed—by following and adjusting care plans according to the evolvement of the disease. In accordance with one or more preferred implementations, systems and methods serve to provide personalized medicine at the point of care—by bringing omics insights and recommendations directly to the point of care. In accordance with one or more preferred implementations, systems and methods serve to proactively manage populations of cancer patients with comprehensive workflow tools. In accordance with one or more preferred implementations, systems and methods allow for continuous learning and improvement of knowledge of cancer using bi-directional feedback between longitudinal patient health records and the omics discoveries. In accordance with one or more preferred implementations, systems and methods serve to standardize knowledge representation of genomics-based diagnosis and classification of cancer.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method executed by a processor of a computing device, the method comprising:
   intercepting, by health information exchange (HIE) software loaded on the computing device, context information from electronic health record (EHR) software loaded on the computing device, the context information including an identification of a patient, the context information intercepted by the HIE software based upon the identification of the patient being displayed in a graphical user interface for the EHR software on a display of the computing device;
   in response to intercepting the context information and based upon the context information, displaying, on an electronic display of the computing device and in an HIE graphical interface for the HIE software, first information for the patient identified in the context information, wherein the graphical interface for the HIE software is displayed concurrently on the display with the graphical interface for the EHR software, and further wherein graphical interface for the EHR software includes second information for the patient that is different from the first information for the patient that is being displayed in the graphical interface for the HIE software;
   receiving, via one or more input devices of the computing device, user input corresponding to engagement with an interface element of the HIE graphical interface;
   in response to receiving the user input, causing a query to be executed over a set of cancer treatment protocols, wherein the query comprises the first information displayed in the HIE graphical interface of the HIE software, and further wherein a cancer treatment protocol is identified from the set of cancer treatment protocols based upon execution of the query over the set of cancer treatment protocols; and
   causing the cancer treatment protocol that was identified based upon execution of the query over the set of cancer treatment protocols to be saved in a unified patient record that is accessible to the HIE software;
   wherein the cancer treatment protocol was identified utilizing a panomics ontology providing cancer stratification by tumor biomarkers.

2. The method of claim 1, wherein the computing device comprises at least one of a touchscreen device, a phone, a mobile device, a desktop computer, or a laptop computer.

3. The method of claim 1, wherein the one or more input devices comprise at least one of a mouse or a keyboard.

4. The method of claim 1, wherein the electronic display comprises a touchscreen, and
   wherein the one or more input devices comprise the touchscreen.

5. The method of claim 4, wherein the computing device comprises at least one of a touchscreen device, a phone, a mobile device, a desktop computer, or a laptop computer.

6. A computing device comprising:
   a processor; and
   memory storing instructions that, when executed by the processor, cause the processor to perform acts comprising:
      intercepting, by health information exchange (HIE) software loaded on the computing device, context information from electronic health record (EHR) software loaded on the computing device, the context information including an identification of a patient, the context information intercepted by the HIE software based upon the identification of the patient being displayed in a graphical user interface for the EHR software on a display of the computing device;
      in response to intercepting the context information and based upon the context information, displaying, on an electronic display of the computing device and in an HIE graphical interface for the HIE software, first information for the patient identified in the context information, wherein the graphical interface for the HIE software is displayed concurrently on the display with the graphical interface for the EHR software, and further wherein graphical interface for the EHR software includes second information for the patient that is different from the first information for the patient that is being displayed in the graphical interface for the HIE software;

receiving, via one or more input devices of the computing device, user input corresponding to engagement with an interface element of the HIE graphical interface;

in response to receiving the user input, causing a query to be executed over a set of cancer treatment protocols, wherein the query comprises the first information displayed in the HIE graphical interface of the HIE software, and further wherein a cancer treatment protocol is identified from the set of cancer treatment protocols based upon execution of the query over the set of cancer treatment protocols; and causing the cancer treatment protocol that was identified based upon execution of the query over the set of cancer treatment protocols to be saved in a unified patient record that is accessible to the HIE software;

wherein the cancer treatment protocol was identified utilizing a panomics ontology providing cancer stratification by tumor biomarkers.

7. The computing device of claim 6 being one of a touchscreen device, a phone, a mobile device, a desktop computer, or a laptop computer.

8. A non-transitory computer-readable medium comprising instructions that, when executed by a processor, cause the processor to perform acts comprising:

intercepting, by health information exchange (HIE) software loaded in the non-transitory computer-readable medium, context information from electronic health record (EHR) software loaded in the non-transitory computer-readable medium, the context information including an identification of a patient, the context information intercepted by the HIE software based upon the identification of the patient being displayed in a graphical user interface for the EHR software on a display of the computing device;

in response to intercepting the context information and based upon the context information, displaying, on an electronic display of a computing device and in an HIE graphical interface for the HIE software, first information for the patient identified in the context information, wherein the graphical interface for the HIE software is displayed concurrently on the display with the graphical interface for the EHR software, and further wherein graphical interface for the EHR software includes second information for the patient that is different from the first information for the patient that is being displayed in the graphical interface for the HIE software;

receiving, via one or more input devices of the computing device, user input corresponding to engagement with an interface element of the HIE graphical interface;

in response to receiving the user input, causing a query to be executed over a set of cancer treatment protocols, wherein the query comprises the first information displayed in the HIE graphical interface of the HIE software, and further wherein a cancer treatment protocol is identified from the set of cancer treatment protocols based upon execution of the query over the set of cancer treatment protocols; and causing the cancer treatment protocol that was identified based upon execution of the query over the set of cancer treatment protocols to be saved in a unified patient record that is accessible to the HIE software;

wherein the cancer treatment protocol was identified utilizing a panomics ontology providing cancer stratification by tumor biomarkers.

9. The non-transitory computer-readable storage medium of claim 8, wherein the computing device is one of a touchscreen device, a phone, a mobile device, a desktop computer, or a laptop computer.

* * * * *